(12) United States Patent
Brozovich et al.

(10) Patent No.: US 8,293,481 B2
(45) Date of Patent: Oct. 23, 2012

(54) BIOMARKERS FOR CHRONIC VASCULAR DYSFUNCTION

(75) Inventors: Frank V. Brozovich, Rochester, MN (US); Frank C. Chen, Rochester, MN (US); Robert P. Frantz, Rochester, MN (US); Ozgur Ogut, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 501 days.

(21) Appl. No.: 12/514,275

(22) PCT Filed: Nov. 2, 2007

(86) PCT No.: PCT/US2007/083468
§ 371 (c)(1),
(2), (4) Date: Jan. 27, 2010

(87) PCT Pub. No.: WO2008/060871
PCT Pub. Date: May 22, 2008

(65) Prior Publication Data
US 2010/0159478 A1    Jun. 24, 2010

Related U.S. Application Data

(60) Provisional application No. 60/865,224, filed on Nov. 10, 2006.

(51) Int. Cl.
*G01N 33/567* (2006.01)
*C12Q 1/68* (2006.01)
(52) U.S. Cl. .......................................... 435/7.1; 435/6.1
(58) Field of Classification Search ........................ None
See application file for complete search history.

(56) References Cited

U.S. PATENT DOCUMENTS

| 5,143,854 | A  | 9/1992 | Pirrung et al. |
| 5,451,683 | A  | 9/1995 | Barrett et al. |
| 5,733,729 | A  | 3/1998 | Lipshutz et al. |
| 5,744,305 | A  | 4/1998 | Fodor et al. |
| 5,770,722 | A  | 6/1998 | Lockhart et al. |
| 2004/0072805 | A1 | 4/2004 | Warren et al. |
| 2004/0167197 | A1 | 8/2004 | Rudolph et al. |

FOREIGN PATENT DOCUMENTS

WO    WO 98/20019    5/1998

OTHER PUBLICATIONS

Abassi et al., "Impaired nitric oxide-mediated renal vasodilation in rats with experimental heart failure: role of angiotensin II," *Circulation*, 1997, 96:3655-3664.
Andersson et al., "Captopril-impaired production of tumor necrosis factor-α-induced interleukin-1βin human monocytes is associated with altered intracellular distribution of nuclear factor-κB," *J Lab Clin Med.*, 2002, 140:103-109.
Awan et al., "Efficacy of ambulatory systemic vasodilator therapy with oral prazosin in chronic refractory heart failure. Concomitant relief of pulmonary congestion and elevation of pump output demonstrated by improvements in symptomatology, exercise tolerance, hemodynamics and echocardiography," *Circulation*, 1977, 56:346-354.
Benson et al., "GenBank," *Nucleic Acids Res.*, 2007, 35:D21-D25.
Boguski et al., "dbEST—database for 'expressed sequence tags'," *Nat. Genet.*, 1993, 4(4):332-333.
Brown et al., "The Rac and Rho Hall of Fame: A decade of hypertrophic signaling hits," *Circ. Res.*, 2006, 98:730-742.
Carson et al., "Racial differences in response to therapy for heart failure: analysis of the vasodilator-heart failure trials," *J. Card Fail.*, 1999, 5(3):178-187.
Chen et al., "Captopril prevents myosin light chain phosphatase isoform switching to preserve normal cGMP-mediated vasodilatation," *J. Mol. Cell. Cardiol.*, 2006, 41(3):488-495.
Chin et al., "Prognostic value of interleukin-6, plasma viscosity, fibrinogen, von Willebrand factor, tissue factor and vascular endothelial growth factor levels in congestive heart failure," *Eur J Clin Invest.*, 2003, 33:941-948
Cohn et al., "Effect of vasodilator therapy on mortality in chronic congestive heart failure. Results of a Veterans Administration Cooperative Study," *N Engl J Med*, 1986, 314:1547-1552.
Conraads et al., "Intracellular monocyte cytokine production and CD14 expression are up-regulated in severe vs mild chronic heart failure," *J Heart Lung Transplant*, 2005, 24:854-859.
Conraads et al., "Type D personality is associated with increased levels of tumour necrosis factor (TNF)-α and TNF-α receptors in chronic heart failure," *Int J Cardiol*, 2006, 113:34-38.
Damas et al., "CXC-chemokines, a new group of cytokines in congestive heart failure—possible role of platelets and monocytes," *Cardiovascular Research*, 2000, 45(2):428-436.
Delp et al., "Changes in skeletal muscle biochemistry and histology relative to fiber type in rats with heart failure," *J Appl Physiol.*, 1997, 83:1291-1299.
Deswal et al., "Cytokines and cytokine receptors in advanced heart failure: an analysis of the cytokine database from the Vesnarinone trial (VEST)," *Circulation*, 2001, 103:2055-2059.
Dirksen et al., "A myosin phosphatase targeting subunit isoform transition defines a smooth muscle developmental phenotypic switch," *Am J Physiol Cell Physiol.*, 2000, 278:C589-C600.
Dzau, "Theodore Cooper Lecture: Tissue angiotensin and pathobiology of vascular disease: a unifying hypothesis," *Hypertension*, 2001, 37:1047-1052.
Francis and Cohn, "Heart failure: mechanisms of cardiac and vascular dysfunction and the rationale for pharmacologic intervention," *FASEB J.*, 1990, 4:3068-3075.
Furchgott, "Endothelium-derived relaxing factor: discovery, early studies, and identification as nitric oxide," *Biosci Rep.*, 1999, 19(4):235-251.
Gibbs et al., "Genome sequence of the Brown Norway rat yields insights into mammalian evolution," *Nature*, 2004, 428(6982):493-521.
Griendling et al., "Angiotensin II stimulates NADH and NADPH oxidase activity in cultured vascular smooth muscle cells," *Circ Res.*, 1994, 74:1141-1148.
Hacia et al., "Detection of heterozygous mutations in BRCA1 using high density oligonucleotide arrays and two—colour fluorescence analysis," *Nature Genet.*, 1996, 14:441-447.

(Continued)

*Primary Examiner* — James Martinell
(74) *Attorney, Agent, or Firm* — Fish & Richardson P.C.

(57) ABSTRACT

Materials and methods for using biomarkers to determine prognosis and response to treatment in subjects having chronic vascular dysfunction.

23 Claims, 1 Drawing Sheet

OTHER PUBLICATIONS

Hartshorne et al., "Myosin light chain phosphatase: subunit composition, interactions and regulation," *J Muscle Res Cell Motil*, 1998, 19:325-341.

Huang et al., "Unzipping the role of myosin light chain phosphatase in smooth muscle cell relaxation," *J Biol Chem*, 2004, 279:597-603.

Hunter et al., "Tumor necrosis factor-α-induced activation of RhoA in airway smooth muscle cells: role in the $Ca^{2+}$ sensitization of myosin light $chain_{20}$ phosphorylation," *Mol Pharmacol*, 2003, 63:714-721.

Isabelle et al., "Role of α1-adrenoreceptors in cocaine-induced NADPH oxidase expression and cardiac dysfunction," *Cardiovasc Res*, 2005, 67699-704.

Jessup and Brozena, "Heart failure," *N Engl J Med*, 2003, 348:2007-2018.

Jin et al., "Effect of early angiotensin-converting enzyme inhibition on Cardiac Gene Expression after acute myocardial infarction," *Circulation*, 2001, 103:736-742.

Johnson and Lincoln, "Effects of nitroprusside, glyceryl trinitrate, and 8-bromo cyclic GMP on phosphorylase a formation and myosin light chain phosphorylation in rat aorta," *Mol Pharmacol*, 1985, 27:333-342.

Jorde et al., "Maximally Recommended Doses of Angiotensin-Converting Enzyme (ACE) Inhibitors Do Not Completely Prevent ACE-Mediated Formation of Angiotensin II in Chronic Heart Failure," *Circulation*, 2000, 101:844-846.

Kaiser et al., "Heart failure depresses endothelium-dependent responses in canine femoral artery," *Am J Physiol*, 1989, 256:H962-H967.

Kandabashi et al., "Inhibition of myosin phosphatase by upregulated rho-kinase plays a key role for coronary artery spasm in a porcine model with interleukin-1α," *Circulation*, 2000, 101:1319-1323.

Karim et al., "Vascular reactivity in heart failure: role of myosin light chain phosphatase," *Circ Res*, 2004, 95:612-618.

Katz et al., "Impaired acetylcholine-mediated vasodilation in patients with congestive heart failure. Role of endothelium-derived vasodilating and vasoconstricting factors," *Circulation*, 1993, 88:55-61.

Khaper and Singal, "Effects of afterload-reducing drugs on pathogenesis of antioxidant changes and congestive heart failure in rats," *J Am Coll Cardiol*, 1997, 29:856-861.

Khatri et al., "Role of myosin phosphatase isoforms in cGMP-mediated smooth muscle relaxation," *J Biol Chem*, 2001, 276:37250-37257.

Konstam, "Improving clinical outcomes with drug treatment in heart failure: what have trials taught?" *Am J Cardiol*, 2003, 91(suppl):9D-14D.

Kobayashi et al., "Critical role of Rho-kinase pathway for cardiac performance and remodeling in failing rat hearts," *Cardiovascular Research*, 2002, 55:757-767.

Kubo et al., "Endothelium-dependent vasodilation is attenuated in patients with heart failure," *Circulation*,1991, 84:1589-1596.

Lai and Frishman, "Rho-Kinase inhibition in the therapy of cardiovascular disease," *Cardiology in Review*, 2005, 13:285-292.

Levine et al., "Elevated circulating levels of tumor necrosis factor in severe chronic heart failure," *N Engl J Med*, 1990, 323:236-241.

Li et al., "Differential effect of hydrogen peroxide and superoxide anion on apoptosis and proliferation of vascular smooth muscle cells," *Circulation*, 1997, 96:3602-3609.

Lincoln et al., "Invited review: cGMP-dependent protein kinase signaling mechanisms in smooth muscle: from the regulation of tone to gene expression," *J Appl Physiol*, 2001, 91:1421-1430.

Livak and Schmittgen, "Analysis of relative gene expression data using real-time quantitative PCR and the $2^{-\Delta\Delta C}T$ Method," *Methods*, 2001, 25(4):402-408.

Mann, "Inflammatory mediators and the failing heart: past, present, and the foreseeable future," *Circ Res*, 2002, 91:988-998.

Miller et al., "Sustained reduction of cardiac impedance and preload in congestive heart failure with the antihypertensive vasodilator prazosin," *N Engl J Med*, 1977, 297:303-307.

Miquel et al., "Acute and chronic captopril, but not prazosin or nifedipine, normalize alterations in adrenergic intracellular Ca2+ handling observed in the mesenteric arterial tree of spontaneously hypertensive rats," *J Pharmacol Exp Ther*, 2005, 313:359-367.

Morgan et al., "Validation of echocardiographic methods for assessing left ventricular dysfunction in rats with myocardial infarction," *Am J Physiol Heart Circ Physiol*, 2004, 287:H2049-H2053.

Negrao et al., "Impaired endothelium-mediated vasodilation is not the principal cause of vasoconstriction in heart failure," *Am J Physiol*, 2000, 278(1):H168-H174.

Nickenig and Harrison, "The AT(1)-type angiotensin receptor in oxidative stress and atherogenesis: part I: oxidative stress and atherogenesis," *Circulation*, 2002, 105:393-396.

Nickenig and Harrison, "The AT(1)-type angiotensin receptor in oxidative stress and atherogenesis: Part II: AT(1) receptor regulation," *Circulation*, 2002, 105:530-536.

Parris et al., "Tumour necrosis factor-α activates a calcium sensitization pathway in guinea-pig bronchial smooth muscle," *J Physiol*, 1999, 518:561-569.

Parthenakis et al., "Relation of cardiac sympathetic innervation to proinflammatory cytokine levels in patients with heart failure secondary to idiopathic dilated cardiomyopathy," *Am J Cardiol*, 2003, 91:1190-1194.

Pfeffer et al., "Effect of captopril on mortality and morbidity in patients with left ventricular dysfunction after myocardial infarction. Results of the survival and ventricular enlargement trial," *N Engl J Med*, 1992, 327(10):669-677.

Pfeffer et al., "Hemodynamic benefits and prolonged survival with long-term captopril therapy in rats with myocardial infarction and heart failure," *Circulation*, 1987, 75(suppl 1):149-155.

Pfeffer et al., "Influence of chronic captopril therapy on the infarcted left ventricle of the rat," *Circ Res*, 1985, 57:84-95.

Sato et al., "Current understanding of biochemical markers in heart failure," *Med Sci Monit*, 2006, 12(11):RA252-RA264.

Selye et al., "Simple techniques for the surgical occlusion of coronary vessels in the rat," *Angiology*, 1960, 11:398-407.

Somlyo and Somlyo, "Ca2+ sensitivity of smooth muscle and nonmuscle myosin II: modulated by G proteins, kinases, and myosin phosphatase," *Physiol Rev*, 2003, 83:1325-1358.

Surks et al., "Regulation of myosin phosphatase by a specific interaction with cGMP-dependent protein kinase Iα," *Science*, 1999, 286:1583-1587.

Suzuki et al., "Time-course of changes in the levels of interleukin 6 in acutely decompensated heart failure," *Int J Cardiology*, 2005, 100:415-420.

Taylor et al., "Combination of isosorbide dinitrate and hydralazine in blacks with heart failure," *N Engl J Med*, 2004, 351(20):2049-2057.

Testa et al., "Circulating level of cytokines and their endogenous modulators in patients with mild to severe congestive heart failure due to coronary artery disease of hypertension," *J Am Coll Cardiol.*, 1996, 28(4):964-971.

Torre-Amione et al., "Proinflammatory cytokine levels in patients with depressed left ventricular ejection fraction: a report from the Studies of Left Ventricular Dysfunction (SOLVD)," *J Am Coll Cardiol*, 1996, 27:1201-1206.

Tsutamoto et al., "Interleukin-6 spillover in the peripheral circulation increases with the severity of heart failure, and the high plasma level of interleukin-6 is an important prognostic predictor in patients with congestive heart failure," *J Am Coll Cardiol.*, 1998, 31:391-398.

Warnholtz et al., "Increased NADH-oxidase-mediated superoxide production in the early stages of atherosclerosis: evidence for involvement of renin-angiotensin system," *Circulation*, 1999, 99:2027-2033.

Wheeler et al., "Database resources of the National Center for Biotechnology," *Nucleic Acids Res*, 2003, 31:28-33.

Winaver et al., "Involvement of Rho kinase pathway in the mechanism of renal vasoconstriction and cardial hypertrophy in rats with experimental heart failure," *Am J Physiol Heart Circ Physiol*, 2006, 290:2007-2014.

Wooldridge et al., "Smooth muscle phosphatase is regulated in vivo by exclusion of phosphorylation of threonine 696 of MYPT1 by phosphorylation of Serine 695 in response to cyclic nucleotides," *J Biol Chem*, 2004, 279:34496-34504.

Yusuf et al., "Effect of enalapril on myocardial infarction and unstable angina in patients with low ejection fractions," *Lancet*, 1992, 340:1173-1178.

Yusuf et al., "Effects of an angiotensin converting-enzyme inhibitor, ramipril, on cardiovascular events in high-risk patients. The Heart Outcomes Prevention Evaluation Study Investigators," *N Engl J Med*, 2000, 342:145-153.

Zafari et al., "Role of NADH/NADPH oxidase-derived H202 in angiotensin II-induced vascular hypertrophy," *Hypertension*, 1998, 32:488-495.

Zalba et al., "Oxidative stress in arterial hypertension: role of NAD(P)H oxidase," *Hypertension*, 2001, 38:1395-1399.

Authorized Officer Kyu Heong Ahn, International Search Report/Written Opinion in PCT/US2007/083468, mailed Mar. 26, 2008, 8 pages.

Authorized Officer Simin Baharlou, International Preliminary Report on Patentability in PCT/US2007/083468, issued May 12, 2009, 6 pages.

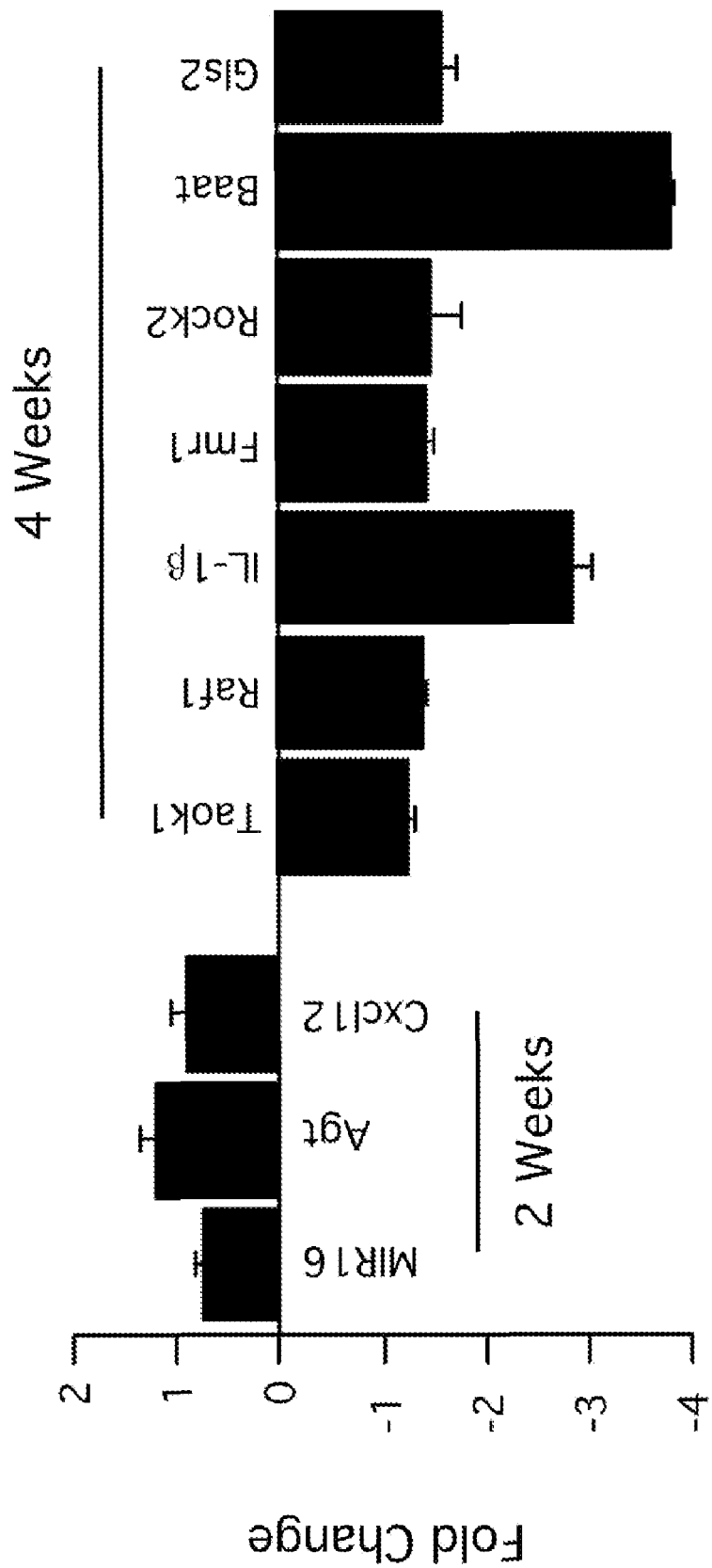

BIOMARKERS FOR CHRONIC VASCULAR DYSFUNCTION

CROSS-REFERENCE TO RELATED APPLICATIONS

This application is a National Stage application under 35 U.S.C. §371 of International Application No. PCT/US2007/083468 having an International Filing Date of Nov. 2, 2007, which claims benefit of U.S. Provisional Application Ser. No. 60/865,224, filed on Nov. 10, 2006, which is incorporated herein by reference in its entirety.

STATEMENT AS TO FEDERALLY SPONSORED RESEARCH

This invention was made with United States government support under grant no. HL069894 awarded by the National Institutes of Health. The U.S. government has certain rights in the invention.

TECHNICAL FIELD

This document relates to materials and methods for assessing the prognosis and response to treatment of individuals with chronic diseases where there is vascular dysfunction, and more particularly to materials and methods for using biomarkers to assess the prognosis and response to treatment of individuals with diseases such as congestive heart failure.

BACKGROUND

Congestive heart failure (CHF; also called chronic heart failure) is a clinical syndrome associated with vascular abnormalities characterized by an elevated baseline vascular tone and impaired response to NO-mediated vasodilatation (Francis and Cohn (1990) *FASEB J.* 4:3068; and Negrao et al. (2000) *Am. J. Physiol.* 278:H168-H174). The mechanism leading to these changes in the vasculature is unknown.

The standard regimen for patients with the clinical syndrome of heart failure consists of a vasodilator (most commonly an angiotensin-converting enzyme (ACE) inhibitor, an angiotensin receptor blocker (ARB) or hydralazine), a β-blocker, a nitrate and, if necessary for volume control, a diuretic. ACE is involved in formation of angiotensin II, which causes constriction of arteries in the body and thereby elevates blood pressure. ACE inhibitors such as captopril (1-[(2S)-3-mercapto-2-methylpropionyl]-L-proline) lower blood pressure by inhibiting the formation of angiotensin II, thus relaxing the arteries. Relaxing the arteries not only lowers blood pressure, but also improves the pumping efficiency of a failing heart and improves cardiac output in patients with heart failure.

Currently, the medication dose required for an individual patient to achieve a clinical response is guided only by clinical expertise. There is no test that can be used to indicate individual patient prognosis and/or response (either beneficial or adverse) to therapy.

SUMMARY

This document is based in part on the discovery of biomarkers that can be evaluated to assess prognosis and/or response to therapy in subjects having CHF. For example, provided herein are methods that include determining the expression level of a gene in a biological sample from the subject, comparing the expression level of the gene in the biological sample to a control expression level of the gene, and determining the prognosis or response to treatment to be favorable or poor based on whether the expression level in the biological sample is lower than, higher than, or similar to the control expression level. The methods provided herein also can be useful to assess a subject's prognosis or response to treatment for other chronic diseases where there is vascular dysfunction, including pulmonary hypertension and erectile dysfunction.

In one aspect, this document features a method for evaluating a subject with a chronic disease where there is vascular dysfunction, comprising assessing in a biological sample from said subject the expression level of TAO kinase I, glutaminase 2 (Gls2), v-raf-1 murine leukemia viral oncogene homolog 1 (Raf1), or bile acid-Coenzyme A amino acid N-acyltransferase (Baat). The disease can be chronic heart failure (CHF). The biological sample can be a blood, serum, saliva, urine, or tissue sample. The expression level can be determined by measuring TAO kinase I, Gls2, Raf1, or Baat mRNA levels in the biological sample, or by measuring TAO kinase I, Gls2, Raf1, or Baat protein levels in the biological sample. The method can further comprise classifying the prognosis of the subject as favorable if the expression level of TAO kinase I, Gls2, Raf1, or Baat in the biological sample is less than a control expression level of TAO kinase I, Gls2, Raf1, or Baat, or classifying the prognosis of the subject as poor if the expression level of TAO kinase I, Gls2, Raf1, or Baat in the biological sample is not less than the control expression level of TAO kinase I, Gls2, Raf1, or Baat. The control expression level can be an expression level in a biological sample from a normal subject, a standard expression level in biological samples from a population of normal subjects, or a previously determined expression level in a biological sample from the subject.

In another aspect, this document features a method for evaluating a subject with a chronic disease where there is vascular dysfunction, comprising assessing in a biological sample from said subject the expression level of interleukin-1β (IL-1β), Rho kinase 2, or fragile X mental retardation syndrome 1 homolog (Fmr1). The disease can be CHF. The biological sample can be a blood, serum, saliva, urine, or tissue sample. The expression level can be determined by measuring interleukin-1β, Rho kinase, or Fmr1 mRNA levels in the biological sample, or by measuring interleukin-1β, Rho kinase, or Fmr1 protein levels in the biological sample. The method can further comprise classifying the prognosis as favorable if the expression level of IL-1β, Rho kinase 2, or Fmr1 in the biological sample is similar to or less than a control expression level of IL-1β, Rho kinase 2, or Fmr1, or classifying the prognosis as poor if the expression level of IL-1β, Rho kinase 2, or Fmr1 in the biological sample is greater than the control expression level of IL-1β, Rho kinase 2, or Fmr1. The control expression level can be an expression level of IL-1β, Rho kinase 2, or Fmr1 in a biological sample from a normal subject, wherein the prognosis is classified as favorable if the expression level in the biological sample is similar to the control expression level, and wherein the prognosis is classified as poor if the expression level in the biological sample is greater than the control expression level. The control expression level can be a standard expression level of IL-1β, Rho kinase 2, or Fmr1 in biological samples from a population of normal subjects, wherein the prognosis is classified as favorable if the expression level in the biological sample is similar to the control expression level, and wherein the prognosis is classified as poor if the expression level in the biological sample is greater than the control expression level. The control expression level can be a previously determined expression level of IL-1β, Rho kinase 2, or Fmr1 in a biological sample from the subject, wherein the prognosis is classified as favorable if the expression level in the biological sample is less than the control expression level, and wherein the prognosis is classified as poor if the expression level in the biological sample is similar to or greater than the control expression level.

In another aspect, this document features a method for assessing the response to treatment of a subject diagnosed as having a chronic disease where there is vascular dysfunction, the method comprising: (a) assessing the expression level of a gene in a biological sample from the subject, wherein the gene is TAOK1, GLS2, RAF1, or BAAT; and (b) classifying the response as favorable if the expression level in the biological sample is less than a control expression level of the gene, or classifying the response as poor if the expression level in the biological sample is not less than the control expression level of the gene. The disease can be CHF. The biological sample can be a blood, serum, saliva, urine, or tissue sample. The expression level can be determined by measuring TAO kinase I, Gls2, Raf1, or Baat mRNA levels in the biological sample, or by measuring TAO kinase I, Gls2, Raf1, or Baat protein levels in the biological sample. The control expression level can be an expression level in a biological sample from a normal subject, a standard expression level in biological samples from a population of normal subjects, or a previously determined expression level in a biological sample from the subject. The treatment can be captopril therapy. The method can further comprise, if the response to treatment is determined to be poor, determining that the treatment dose should be increased.

In another aspect, this document features a method for assessing the response to treatment of a subject diagnosed as having a chronic disease where there is vascular dysfunction, the method comprising: (a) assessing the expression level of a gene in a biological sample from the subject, wherein the gene is IL-1β, ROCK2, or FMR1; and (b) classifying the response as favorable if the expression level in the biological sample is similar to or less than a control expression level of the gene, or classifying the response as poor if the expression level in the biological sample is greater than the control expression level of the gene. The disease can be CHF. The biological sample can be a blood, serum, saliva, urine, or tissue sample. The expression level can be determined by measuring IL-1β, Rho kinase 2, or Fmr1 mRNA levels in the biological sample, or by measuring IL-1β, Rho kinase 2, or Fmr1 protein levels in the biological sample. The control expression level can be an expression level in a biological sample from a normal subject, wherein the response is classified as favorable if the expression level in the biological sample is similar to the control expression level of the gene, and wherein the response is classified as poor if the expression level in the biological sample is greater than the control expression level of the gene. The control expression level can be a standard expression level in biological samples from a population of normal subjects, wherein the response is classified as favorable if the expression level in the biological sample is similar to the control expression level of the gene, and wherein the response is classified as poor if the expression level in the biological sample is greater than the control expression level of the gene. The control expression level can be a previously determined expression level in a biological sample from the subject, wherein the response is classified as favorable if the expression level in the biological sample is less than the control expression level of the gene, and wherein the response is classified as poor if the expression level in the biological sample is similar to or greater than the control expression level of the gene. The treatment can be captopril therapy. The method can further comprise, if the response to treatment is determined to be poor, determining that the treatment dose should be increased.

This document also features a method for evaluating a subject with a chronic disease where there is vascular dysfunction, comprising assessing in a biological sample from said subject the expression level of membrane interacting protein of RGS16 (Mir16), angiotensinogen (Agt), or chemokine (C-X-C motif) ligand 12 (Cxcl12). The disease can be CHF. The biological sample can be a blood, serum, saliva, urine, or tissue sample. The expression level can be determined by measuring Mir16, Agt, or Cxcl12 mRNA levels in the biological sample, or by measuring Mir16, Agt, or Cxcl12 protein levels in the biological sample. The method can further comprise classifying the prognosis of the subject as favorable if the expression level of Mir16, Agt, or Cxcl12 in the biological sample is greater than or similar to a control expression level of Mir16, Agt, or Cxcl12, or classifying the prognosis as poor if the expression level of Mir16, Agt, or Cxcl12 in the biological sample is less than a control expression level of Mir16, Agt, or Cxcl12. The control expression level can be an expression level of Mir16, Agt, or Cxcl12 in a biological sample from a normal subject, wherein the prognosis is classified as favorable if the expression level in the biological sample is similar to the control expression level, and wherein the prognosis is classified as poor if the expression level in the biological sample is less than the control expression level. The control expression level can be a standard expression level of Mir16, Agt, or Cxcl12 in biological samples from a population of normal subjects, wherein the prognosis is classified as favorable if the expression level in the biological sample is similar to the control expression level, and wherein the prognosis is classified as poor if the expression level in the biological sample is less than the control expression level. The control expression level can be a previously determined expression level of Mir16, Agt, or Cxcl12 in a biological sample from the subject, wherein the prognosis is classified as favorable if the expression level in the biological sample is greater than the control expression level, and wherein the prognosis is classified as poor if the expression level in the biological sample is less than or similar to the control expression level.

In still another aspect, this document features a method for assessing the response to treatment of a subject diagnosed as having a chronic disease where there is vascular dysfunction, the method comprising: (a) assessing the expression level of a gene in a biological sample from the subject, wherein the gene is MIR16, AGT, or CXCL12; and (b) classifying the response as favorable if the expression level in the biological sample is similar to or greater than a control expression level of the gene, or classifying the response as poor if the expression level in the biological sample is less than the control expression level of the gene. The disease can be CHF. The biological sample can be a blood, serum, saliva, urine, or tissue sample. The expression level can be determined by measuring Mir16, Agt, or Cxcl12 mRNA levels in the biological sample, or by measuring Mir16, Agt, or Cxcl12 protein levels in the biological sample. The control expression level can be an expression level in a biological sample from a normal subject, wherein the response is classified as favorable if the expression level in the biological sample is similar to the control expression level of the gene, and wherein the response is classified as poor if the expression level in the biological sample is less than the control expression level of the gene. The control expression level can be a standard expression level in biological samples from a population of normal subjects, wherein the response is classified as favorable if the expression level in the biological sample is similar to the control expression level of the gene, and wherein the response is classified as poor if the expression level in the biological sample is less than the control expression level of the gene. The control expression level can be a previously determined expression level in a biological sample from the subject, wherein the response is classified as favorable if the expression level in the biological sample is greater than the control expression level of the gene, and wherein the response is classified as poor if the expression level in the biological sample is similar to or less than the control expression level of the gene. The treatment can be captopril therapy. The method can further comprise, if the response to treatment is determined to be poor, determining that the treatment dose should be increased.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the description below. Other features, objects, and advantages of the invention will be apparent from the description and drawing, and from the claims.

BRIEF DESCRIPTION OF THE DRAWING

FIG. 1 is a bar graph demonstrating fold change (mean±SEM) in gene expression between captopril and placebo treated groups at 2 weeks (MIR16, Agt, Cxcl12) and 4 weeks (Taok1, Raf1, IL-1β, Fmr1, Rock2, Baat, Gls2) following LAD ligation. Abbreviations: MIR16, membrane interacting protein of RGS16; Agt, angiotensinogen; Cxcl12, chemokine (C-X-C motif) ligand 12; Taok1, TAO kinase 1; Raf1, v-raf-1 murine leukemia viral oncogene homolog 1; IL-1β, interleukin 1 beta; Fmr1, fragile X mental retardation syndrome 1 homolog; Rock2, Rho kinase 2; Baat, bile acid-Coenzyme A amino acid N-acyltransferase; Gls2, glutaminase 2 (liver, mitochondrial).

DETAILED DESCRIPTION

The materials and methods disclosed herein can be used to assess disorders where there is vascular dysfunction (e.g., CHF, erectile dysfunction, and pulmonary hypertension) in affected individuals. For example, this document provides materials and methods for assessing prognosis and/or response to treatment in an individual diagnosed as having CHF. CHF has a 5-year mortality rate that approaches 50%. As used herein, "prognosis" refers to the likelihood of succumbing to CHF, where a "poor prognosis" indicates a high chance of death and a "favorable prognosis" indicates a low chance of death. As used herein, "response to treatment" refers to the clinical response of an individual treated for a disorder such as CHF, where a "poor response to treatment" indicates that an individual's disease status has not improved (e.g., has not changed or has worsened) after treatment, while a "favorable response to treatment" indicates that the individual's disease status has improved after treatment.

The methods provided herein include evaluating the expression level of one or more biomarkers in an individual having chronic vascular dysfunction, and comparing the expression level to a control expression level of that marker. A control expression level of a biomarker can be, for example, the expression level of the biomarker in a normal individual, a standardized level of expression of the biomarker (e.g., a standard level determined by averaging the expression level in a plurality of normal individuals), or the expression level of the biomarker in the affected individual determined prior to treatment or at an earlier time point after the onset of treatment (e.g., treatment with an ACE inhibitor or other vasodilator, a nitrate, a β-blocker, a diuretic, or a combination thereof).

The expression level of one or more of the biomarkers listed herein typically is evaluated in a biological sample obtained from a subject having a disorder such as CHF. As used herein, a "biological sample" is a sample that contains cells or cellular material, from which nucleic acids or polypeptides can be obtained. Non-limiting examples of biological samples include urine, blood, cerebrospinal fluid, pleural fluid, sputum, and peritoneal fluid, bladder washings, secretions (e.g. breast secretion), oral washings, swabs (e.g., oral swabs), tissue samples, touch preps, or fine-needle aspirates.

The level of expression from a particular gene can be determined using any suitable method. For example, the level of expression from a particular gene can be assessed by measuring the level of mRNA expression from the gene. Levels of mRNA expression can be evaluated using, without limitation, northern blotting, slot blotting, quantitative reverse transcriptase polymerase chain reaction (RT-PCR), or chip hybridization techniques, all of which are known in the art. Chip hybridization assays can be particularly useful, as they can be used to simultaneously determine the relative expression levels of multiple mRNAs. In some embodiments, the level of expression from a particular gene can be assessed by measuring polypeptide levels. Polypeptide levels can be measured using any method such as immuno-based assays (e.g., ELISA), western blotting, protein arrays, or silver staining.

The biomarkers that can be evaluated in the methods provided herein include the TAOK1 gene, which encodes TAO kinase 1; interleukin-1β (IL-1β); the ROCK2 gene, which encodes Rho kinase; the GLS2 gene, which encodes glutaminase 2 (liver, mitochondrial); the RAF1 gene, which encodes the mitogenic Raf-1 MAP kinase kinase kinase (MAP3K) protein; the AGT gene, which encodes angiotensinogen; the CXCL12 gene, which encodes chemokine (C-X-C motif) ligand 12; the MIR16 gene, which encodes a putative membrane glycerophosphodiester phosphodiesterase that may mediate lipid metabolism and G protein signaling; the BAAT gene, which encodes bile acid Coenzyme A amino acid N-acyltransferase (glycine N-choloyltransferase); and the FMR1 gene, which encodes the Fragile X mental retardation 1 protein that is thought to be involved in mRNA trafficking and/or localization.

The methods provided herein can be used to assess the prognosis of an individual diagnosed with a vascular dysfunction disorder such as CHF, and can include, for example, assessing the expression level of a gene in a biological sample from the subject, and classifying the prognosis as favorable or poor based on whether the expression level in the biological sample is less than, similar to, or greater than a control expression level of the gene. Methods provided herein also can be used to determine the response of an individual having a vascular dysfunction disorder (e.g., CHF) to treatment for the condition. Such methods can include, for example, assessing the expression level of a gene in a biological sample from the subject, and classifying the response as favorable or poor based on whether the expression level in the biological sample is less than, similar to, or greater than a control expression level of the gene.

As used herein, the phrase "less than" with respect to gene expression refers to a level of expression that is lower than a control level of expression by at least about 5% (e.g., 5%, 10%, 15%, 20%, 25%, or more than 25%). The phrase "similar to" with respect to gene expression refers to a level of expression that is within about 5% (e.g., within 5%, 4%, 3%, 2%, or 1%) of a control level of expression. The phrase "greater than" with respect to gene expression refers to a level of expression that is higher than a control level of expression by at least about 5% (e.g., 5%, 10%, 15%, 20%, 25%, 50%, 100%, or more than 100%). It is noted that the phrases "not less" and "not less than" encompass both "similar to" and "greater than," while the phrases "not greater" and "not greater than" encompass both "similar to" and "less than."

Typically, if expression of one of the above biomarkers is at a level that is less than the expression level in a control sample (e.g., a sample from a normal individual, or a sample obtained from the affected individual prior to treatment or at an earlier time point after the onset of treatment) a favorable prognosis and/or a favorable response to treatment is indicated. Conversely, if expression of one of the above biomarkers is at a level that is greater than the expression level in a control sample (e.g., a sample from a normal individual, or a sample obtained from the affected individual prior to treatment or at an earlier time point after the onset of treatment) a poor prognosis and/or a poor response to treatment is indicated. In some cases, depending on the biomarker evaluated, a level of gene expression that is similar to a control level (e.g., where the control is a level of gene expression in a sample from a normal individual or is a standard level of gene expression based on a plurality of normal individuals) can indicate a favorable prognosis or response to treatment. In other cases, a level of gene expression that is similar to a control level (e.g., where the control is a level of gene expression in a sample obtained from an individual at an earlier time point) can indicate a poor prognosis or response to treatment.

For example, if the level of expression of Raf1, Gls2, Taok 1, or Baat in a biological sample from an individual having CHF is less than the level of expression of the same gene in a control sample, the individual can be said to have a favorable prognosis and, if the individual is undergoing treatment, to have a favorable response to the treatment. Conversely, if the level of expression of Raf1, Gls2, Taok 1, or Baat in a biological sample from an individual having CHF is not less than (i.e., greater than or similar to) the level of expression of the same gene in a control sample, the individual can be said to have a poor prognosis and, if the individual is undergoing treatment, to have a poor response to the treatment. Further, if the level of expression of Fmr1, IL-1β, or Rock2 in a biological sample from an individual having CHF is less than or similar to the level of expression of the same gene in a control sample, the individual can be said to have a favorable prognosis and, if the individual is undergoing treatment, to have a favorable response to the treatment. Conversely, if the level of expression of Fmr1, IL-1β, or Rock2 in a biological sample from an individual having CHF is greater than the level of expression of the same gene in a control sample, the individual can be said to have a poor prognosis and, if the individual is undergoing treatment, to have a poor response to the treatment. Additionally, if the level of expression of Mir16, Agt, or Cxcl12 in a biological sample is similar to the expression of the same gene in a control sample, the individual can be said to have a favorable prognosis, and if the patient is undergoing treatment, to have a favorable response to the therapy. On the other hand, if the level of expression of Mir16, Agt, or Cxcl12 in a biological sample is lower than the expression of the same gene in a control sample, the individual can be said to have a poor prognosis, and if the patient is undergoing treatment, to have a poor response to the therapy.

The methods provided herein also can be used to determine whether the dose of a treatment for CHF should be adjusted. For example, if the level of expression of Raf1, Taok 1, or Baat in a biological sample from an individual treated for CHF is greater than or similar to the level of expression of the same gene in a control sample (e.g., a control biological sample obtained from the individual at an earlier time point), the response to treatment can be deemed poor, indicating that the treatment dose may need to be increased. Similarly, if the level of expression of Fmr1, IL-1β, or Rock2 in a biological sample from an individual treated for CHF is greater than the level of expression of the same gene in a control sample, the response to treatment can be deemed poor, indicating that the treatment dose may need to be increased. Additionally, if the level of expression of Mir16 in a biological sample from an individual treated for CHF is less than the level of expression of the same gene in a control sample, the response to treatment can be deemed poor, indicating that the treatment dose may need to be increased. Conversely, a response to therapy that is deemed favorable can indicate that the treatment can be maintained at current levels, or even that the treatment dose can be decreased.

Also provided herein are articles of manufacture, which can include populations of isolated nucleic acid molecules or polypeptides immobilized on a substrate. The polypeptides or nucleic acids can include two or more of the biomarkers disclosed herein, such that the arrays can be used to determine the prognosis or response to treatment of an individual having a vascular dysfunction disorder such as CHF. Suitable substrates provide a base for the immobilization of the nucleic acids or polypeptides, and in some embodiments, allow immobilization of nucleic acids or polypeptides into discrete regions. In embodiments in which the substrate includes a plurality of discrete regions, different populations of isolated nucleic acids or polypeptides can be immobilized in each discrete region. Thus, each discrete region of the substrate can include a different nucleic acid or polypeptide. Such articles of manufacture can include two or more of the biomarkers disclosed herein, or can include all of the biomarkers disclosed herein.

Suitable substrates can be of any shape or form and can be constructed from, for example, glass, silicon, metal, plastic, cellulose, or a composite. For example, a suitable substrate can include a multiwell plate or membrane, a glass slide, a chip, or polystyrene or magnetic beads. Nucleic acid molecules or polypeptides can be synthesized in situ, immobilized directly on the substrate, or immobilized via a linker, including by covalent, ionic, or physical linkage. Linkers for immobilizing nucleic acids and polypeptides, including reversible or cleavable linkers, are known in the art. See, for example, U.S. Pat. No. 5,451,683 and WO98/20019. Immobilized nucleic acid molecules typically are about 20 nucleotides in length, but can vary from about 10 nucleotides to about 1000 nucleotides in length.

In practice, a sample of DNA or RNA from a subject can be amplified, the amplification product hybridized to an article of manufacture containing populations of isolated nucleic acid molecules in discrete regions, and hybridization can be detected. Typically, the amplified product is labeled to facilitate detection of hybridization. See, for example, Hacia et al.

(1996) Nature Genet. 14:441-447; and U.S. Pat. Nos. 5,770,722 and 5,733,729. Any method can be use to attach nucleic acids and polypeptides to a substrate in the preparation of an array. For example, spotting techniques and in situ synthesis techniques can be used to make arrays. Further, nucleic acid arrays can be prepared using methods such as those disclosed in U.S. Pat. Nos. 5,744,305 and 5,143,854.

In addition to materials and methods for determining prognosis and response to treatment of individuals having vascular dysfunction disorders such as CHF, this document also provides materials and methods for identifying molecules targeted to Acot8 (acyl-CoA thioesterase 8), which is thought to be involved in regulating fatty acid breakdown and the level of acetyl-CoA in cells. As discussed in the Examples below, levels of Acot8 were down-regulated in a rat model of CHF. Thus, molecules that are targeted to Acot8 and can result in increased levels of Acot8, or increased Acot8 activity, may be useful to treat chronic diseases where there is vascular dysfunction.

Compounds that increase Acot8 levels or Acot8 activity can be identified using in vitro or in vivo methods, or combinations of in vitro and in vivo methods. For example, a compound that increases Acot8 levels can be identified by contacting a cell in vitro with a test compound, and then assessing the level of Acot8 nucleic acid or protein. Compounds may affect Acot8 levels or activity either directly or indirectly (e.g., by affecting an upstream molecule). Test compounds can include, for example, small molecules, glycoproteins, polysaccharides, polypeptides, and nucleic acids. Any suitable cell type can be used. For example, cell lines such as human embryonic kidney cells (e.g., HEK293 cells), muscle cell lines, or adipocyte cell lines can be used, or primary cell cultures can be used. Compounds shown to increase Acot8 levels or activity can be administered to a non-human subject for in vivo studies. Alternatively, test compounds can be directly administered to a non-human subject. Suitable non-human subjects include, for example, rodents such as rats and mice, rabbits, guinea pigs, farm animals such as pigs, turkeys, cows, sheep, goats, or chickens, or household pets such as dogs or cats.

Acot8 activity can be monitored using any suitable method. For example, Acot8 activity can be monitored by measuring fatty acid or acetyl-CoA levels in a cell to which a test compound has been administered. Compounds that increase Acot8 levels and/or activity can be administered to a non-human subject, and fatty acid or acetyl-CoA levels of the subject can be compared to that of a control subject (e.g., a corresponding non-human subject to which the test compound was not administered, or to the baseline fatty acid or acetyl-CoA level of the subject).

The invention will be further described in the following examples, which do not limit the scope of the invention described in the claims.

EXAMPLES

Example 1

Materials and Methods

Rat model of congestive heart failure: A surgically induced infarct model of CHF was used (Chen et al. (2006) *J. Mol. Cell. Cardiol.* 41:488-495). Briefly, adult male Sprague-Dawley rats (Harlan, Indianapolis, Ind.) weighing 350-400 g were put under general anesthesia by induction with vaporized isoflurane (3%/volume mixture) and subsequently intubated via direct laryngoscopy. After intubation, rats were ventilated continuously (room air) using a small animal ventilator (Model 683, Harvard Apparatus, Holliston, Mass.). A left lateral thoracotomy incision was made along the $5^{th}$ intercostal space and after the pericardium was opened, the heart was exteriorized using a retention suture placed at the apex. The left anterior descending coronary artery (LAD) was ligated twice using 6-0 prolene suture (Ethicon, Cornelia, Ga.). After chest closure with running 3-0 vicryl suture (Ethicon), rats were put in a recovery chamber with a heating pad and warming light. The post-operative survival rate reached 80%.

Beginning on post-operative day 1, rats were allowed to drink ad libitum, with one group given a solution of captopril in water (2 g/l) and the other group given placebo (water only). Rats were fed a standard diet of Teklad rodent feed (Harlan) ad libitum and kept on a 12:12 h light-dark cycle. Rats were sacrificed at designated time intervals of 2 weeks and 4 weeks after surgery. On average, the animals drank approximately 20 ml of water daily, which is 100 mg/kg/day of captopril.

Determination of left ventricular function: All rats in the placebo and captopril treated groups underwent transthoracic echocardiography (Acuson Sequoia C256® Echocardiography System, Siemens, Malvern, Pa.) at baseline prior to LAD ligation and at 2 and 4 weeks after LAD ligation, using 2-D digital loop imaging under conscious sedation with vaporized isoflurane (2%/volume mixture) as previously described (Morgan et al. (2004) *Am. J. Physiol.* 287:H2049-H2053]. Both parasternal long and short axis views were obtained using a 13-MHz linear array transducer. Digital calipers were used to measure end systolic dimension (ESD) and end diastolic dimension (EDD). Cardiac function was estimated using fractional shortening (FS) obtained from the EDD and ESD in the parasternal long axis view and calculated as FS=((EDD−ESD)/EDD)×100%.

Determination of the dose-response relationship to cGMP: Aortic smooth muscle strips were isolated from rats in the uninfarcted control group without treatment and from both placebo as well as captopril treated group at 2 weeks and 4 weeks post-LAD ligation to determine the dose-response relationship to cGMP. Methods for tissue preparation and composition of all solutions were as described previously (Karim et al. (2004) *Circ. Research* 95:612-618). Briefly, after isolation, the aorta was placed immediately in cold $Ca^{2+}$ free physiological saline solution (in mM: NaCl, 140; KCl, 4.7; $Na_2HPO_4$, 2.25; KCl, 1.2; d-glucose, 5.6; MOPS, 2; EDTA, 0.5; pH, 7.4) and removed of surrounding connective tissues. Subsequently, aortic smooth muscle strips of 200 to 500 µm in length, 100 to 200 µm in width, and approximately 100 µm in thickness were prepared and clamped at both ends with aluminum foil T-clips. The tissues were transferred to a mechanics workstation (Aurora Biosciences, Ontario, Canada), where they were mounted between a piezoresistive force transducer (Sensor One, San Francisco, Calif.) and a length driver (Aurora Biosciences, Ontario, Canada). The tissue strips were then stretched to $L_o$ (i.e., the length for optimum force production) and stimulated to contract with a solution containing 80 mM KCl (in mM: NaCl, 64.7; KCl, 80; $MgSO_4$, 1.2; $CaCl_2$, 1.6; $NaH_2PO_4$, 1.2; MOPS, 2.0; d-glucose, 5.0; EDTA, 0.2; pH, 7.4). After the force reached a steady state, the dose-response relationship to 8-Br-cGMP (Calbiochem, San Diego, Calif.) was determined. The maximal force for each contraction was set to 100%, and the relaxation produced by 8-Br-cGMP was expressed as a percent of the maximal force.

Isolation of total RNA: Tissue from the aorta (30 mg) and portal vein (30 mg) were harvested from each rat. Surrounding peri-adventitial tissues, fat, and endothelium were then carefully cleaned away and removed. The remaining vascular smooth muscle was then frozen with liquid nitrogen, pulverized into fine powder, and resuspended in 600 µl of Buffer RLT with β-ME (10 µl β-ME: 1 ml Buffer RLT, Qiagen, Valencia, Calif.). The lysate was pipetted directly onto a QIAshredder spin column (Qiagen) placed in a 2 ml collection tube and centrifuged for 5 minutes at 14000 rpm, 4° C. The supernatant was transferred to a new microcentrifuge tube and 1 volume of 70% ethanol was added and mixed. The cleared lysate was then transferred to an RNeasy mini-column (Qiagen) placed in a 2 ml collection tube and spun for 15 seconds at ≧10,000 rpm, 4° C. The flow-through was discarded and 700 µl of Buffer RW1 (Qiagen) was added to the RNeasy column. After the column was spun for 15 seconds at ≧10,000 rpm (4° C.), it was transferred into a new 2 ml collection tube, washed, spun twice with 500 µl Buffer RPE (Qiagen), and eluted with 40 µl of RNase-free water using a microcentrifuge (≧10,000 rpm, 4° C.) for 1 minute. Final RNA samples were stored at −20° C. to prevent degradation.

Measurement of RNA concentration: RNA samples were diluted (1/50) with RNase-free water to a total volume of 500 µl, and pipetted into 1 ml cuvettes. The concentration of RNA was determined by measuring the absorbance at 260 nm ($A_{260}$) in a spectrophotometer (Shimadzu Corporation). The final concentration of RNA (µg/ml) was calculated using the formula $40 \times A_{260} \times 50$ (dilution factor).

Determination of gene expression using Affymetrix microarrays: Gene expression analysis was conducted using a GeneChip Rat Genome 230 2.0 Array (Affymetrix, West Sacramento, Calif.), with sequences selected from the GENBANK® (World Wide Web at ncbi.nlm.nih.gov) database for expressed sequence tags (dbEST), and Reference Sequence (RefSeq) (Benson et al. (2007) *Nucleic Acids Res.* 35:D21-25; and Boguski et al. (1993) *Nat. Genet.* 4:332-333). These sequence clusters were created from the UniGene database (Wheeler et al. (2003) *Nucleic Acids Res.* 31:28-33; Build 99, June 2002, World Wide Web at ncbi.nlm.nih.gov) and then refined by analysis and comparison with the publicly available draft assembly of the rat genome from the Baylor College of Medicine Human Genome Sequencing Center (Gibbs et al. (2004) *Nature* 428:493-521). Oligonucleotide probes complementary to each corresponding sequence were synthesized in situ on the arrays; eleven pairs of oligonucleotide probes were used to measure the level of transcription of each sequence represented on the GeneChip Rat Genome 230 2.0 Array. GENECHIP® Scanner 3000 and GENECHIP® Operating Software (GCOS) v1.1.1 (Affymetrix, West Sacramento, Calif.), enabled for high-resolution scanning, was used for the final microarray analysis. Differentially expressed genes are listed according to their GeneID number in the National Center for Biotechnology Information (NCBI) database.

To ensure accurate analysis, a minimum of 3 ng of good quality total RNA at a concentration of ≧500 pg/µl was required. RNA (1 ng) was tested for its quality using an Agilent 2100 bioanalyzer (Agilent Technologies). A RNA Integrity Number (RIN) was assigned to each sample, and RIN ≧6 was considered satisfactory for proceeding with the microarray analysis.

Confirmation of microarray result by quantitative real-time PCR: The remaining RNA from the aortic or portal vein RNA sample was quantitatively converted to single stranded cDNA using the High-Capacity cDNA Archive Kit (Applied Biosystems, Foster City, Calif.). Briefly, 50 µl of RNA sample was mixed with 50 µl of 2×RT master mix (10 µl of 10× Reverse Transcription Buffer, 4 µl of 25× dNTPs, 10 µl of 10× random primers, 5 µl of MULTISCRIBE™ Reverse Transcriptase at 50 U/µl, 21 µl of RNase-free $H_2O$) and pipetted into 0.2 ml MICROAMP® PCR Reaction Tubes with Caps (Applied Biosystems, Foster City, Calif.). Reverse transcription was performed using a thermal cycler (Eppendorf Mastercycler gradient) with incubation conditions set at 25° C. for 10 minutes followed by 37° C. for 120 minutes.

The synthesized cDNA was then mixed with TAQMAN® Universal PCR Master Mix (2.5 µl of cDNA+47.5 µl of RNase-free $H_2O$+50 µl of Master Mix) and loaded onto 384-Well micro fluid cards for quantitative real-time PCR (TAQMAN® Low Density Arrays, Applied Biosystems). This was done with customer-selected TAQMAN® Gene Expression Assays preloaded into each of the 384 wells. The 7900 HT Gene Expression Micro Fluid Card Configuration 2 (Applied Biosystems) with a total of 24 targets was used; 22 targets were selected to include the results from the microarray study, and the remaining two targets were controls GAPDH and 18S controls. For each cDNA sample, four replicates were analyzed for real-time PCR. After all ports of the Micro Fluidic Card were loaded with cDNA, it was spun for even distribution into the wells using a Sorvall Legend centrifuge (1 minute at 1200 rpm). The array was then run on the Applied Biosystems 7900HT Fast Real-time PCR System, and the data were analyzed using an Applied Biosystems RQ Manager Software (SDS 2.1).

For real-time PCR analysis, a relative quantification method was used in which the PCR signal of the designated target transcript in the infarct group with or without captopril therapy was compared to that of the baseline uninfarcted control. The amount of RNA added was normalized to an internal control, GAPDH (which did not change with MI or captopril treatment), and then calibrated to the untreated and uninfarcted baseline control. Data are presented as the fold change in gene expression normalized to the endogenous reference gene and relative to the uninfarcted control using the derived $2^{-\Delta\Delta C_T}$ method (Livak and Schmittgen (2001) *Methods* 25:402-408). The relative change in gene expression was calculated from the relative quantification (RQ) number analyzed from the RQ Manager Software using the formula (RQ−1/RQ=Δ in %), for which a 100% increase represents a 2-fold increase in expression, while a 50% decrease is a 2-fold decrease in expression.

Statistics: The Affymetrix array was used to determine gene expression at 2 weeks and 4 weeks. Uninfarcted control aorta was then compared with both captopril and placebo treated aorta. Similarly, uninfarcted control portal vein was compared with both captopril and placebo treated portal vein. The genes identified for the comparison of aorta with captopril therapy and placebo treatment had P=0.017 and a fold change of 1.22-1.67. These identified genes, as well as additional genes known to activate MYPT1 pathways identified using Ingenuity Pathway Analysis (Ingenuity Systems), were loaded as targets for real-time PCR confirmation.

For real-time PCR, the data were reported as RQ number (mean±SEM). There was a baseline uninfarcted control group (n=3), and at each time point, there were two groups (infarct only, n=3 vs. infarct+captopril, n=3). Data were not pooled, and for each animal each sample was run in triplicate for both microarray gene expression and real-time PCR. Differences between the means were determined using an ANOVA and Tukey's Honestly Significantly Different Test, and P<0.05 was reported as significant.

Example 2

LV Function

Following the induction of an acute myocardial infarction, left ventricular function fell in both placebo and captopril treated animals. In the control, uninfarcted rats fractional shortening (FS) was 56%. In the placebo treated animals after LAD ligation, FS significantly decreased by 2 weeks post-infarction (29%, P<0.05) and remained depressed at 4 weeks post-surgery. Treatment with captopril attenuated the fall in FS and hence improved left ventricular function (LVF); at 2 weeks post-infarction, FS was 38%.

Example 3 cGMP Mediated Smooth Muscle Relaxation

Smooth muscle from the uninfarcted rats, in comparison to placebo treated infarcted rats with depressed LVF, was significantly (P<0.05) more sensitive to cGMP-mediated relaxation. For aortic smooth muscle strips from the post-infarct animals treated with captopril (at both 2 and 4 weeks), the sensitivity of cGMP-mediated relaxation was not different (P>0.05) from the uninfarcted control aorta.

Example 4

Gene Expression

DNA microarrays were used for analysis of the entire rat genome with the criteria set forth above (see Statistics), comparing aorta at baseline (uninfarcted rats) to 2 weeks post-infarction with and without captopril therapy. These studies revealed the differential expression of 11 genes. Five genes are known: acyl-CoA thioesterase (ACOT8), afadin (Af6), glycerophosphodiester phosphodiesterase (MIR16), TAO kinase 1 (Taok1), and Sel (suppressor of lin-12) 1 homolog 1h. (Sel1h). Four are expressed sequence tags (ESTs), which mapped to predicted gene loci (GeneID 297481, GeneID 366480, GeneID 312710, and GeneID 289233). The other 2 genes are ESTs with only the corresponding Affymetrix gene probe identification numbers (1382944_at and 1373690_at). By clustering algorithms, the gene expression profile for aorta at 2 weeks post-infarction with and without captopril were similar, and thus formed a distinct group cluster compared to the control aorta. For the five known differentially expressed genes, aortic expression level at 2 weeks was higher in both infarcted rats with or without captopril than control rats without surgery. One additional differentially expressed gene (LOC297481, GeneID 297481) mapped to the predicted gene locus of the eukaryotic translation initiation factor 4E (eIF4E) member 3.

The portal vein at 2 weeks after surgery also showed distinct group clustering as compared to the baseline control portal vein, and the portal vein formed a distinct group cluster compared to the aorta. However, expression did not vary significantly among infarcted versus non-infarcted groups or treatment versus non-treatment groups, except for Af6, which revealed increased expression in post-MI groups versus the non-infarcted control.

Comparison of aortic tissue at baseline without infarction to the groups 4 weeks post-infarction with or without captopril demonstrated differential expression of 10 genes. For the 10 differentially expressed genes, 7 are known genes and the other 4 are ESTs. Four genes, including cytochrome c oxidase subunit Va (Cox5a), trafficking protein particle complex 1 (Trappc1), CCAAT/enhancer binding protein (C/EBP) gamma (Cebpg), and regulated endocrine-specific protein 18 (Resp18) showed higher expression with surgery and a further increase in expression with captopril therapy in the aorta. Two genes, chemokine (C-X-C motif) ligand 12 (Cxcl12) and trimethyllysine hydroxylase epsilon (Tmlhe), showed increased expression at 4 weeks with captopril in the aorta, but in the surgery group without treatment, expression in the aorta was less than the baseline control. For glutaminase 2 (Gls2), expression in the aorta was the lowest in the captopril treated group at 4 weeks and highest in the infarct group without therapy. Cluster analysis of the heat maps for the aorta at 4 weeks post-surgery revealed that captopril treated and baseline (uninfarcted) formed a distinct group cluster when compared to aorta at 4 weeks post-infarction without captopril. These data demonstrate that captopril therapy results in a change of gene expression in aortic tissue from 2 weeks (where the post infarct groups are similar) to 4 weeks (where control and captopril groups are similar).

For the portal vein at 4 weeks post-infarction, there was no significant change in expression for genes that showed a difference with captopril therapy in the aorta, except Resp18, which demonstrated decreased expression post-infarction.

Real time PCR was used to verify these results. For the aorta, the 12 known genes identified with the microarray (5 genes at 2 weeks and 7 genes at 4 weeks) and an additional 10 genes known to activate MYPT1 pathways identified using Ingenuity Pathway Analysis (Ingenuity Systems) were further analyzed. At 2 weeks post MI (Table 1), there were a total of 8 genes that showed significant changes in expression in the post MI groups compared to the uninfarcted control aorta. In particular, expression of IL-1β, Agt, Cxcl12, and Sel1h was significantly higher post infarction, expression of Acot8, Cox5a, and HGF was depressed in the post infarction groups, and expression of MIR16 was decreased only in the placebo treatment group. Comparing the two post-MI groups, captopril therapy significantly increased expression of MIR16, Agt, and Cxcl12. At 2 weeks post infarction, there was no significant change in the expression of 14 genes (Taok1, Raf1, Fmr1, Rock2, Baat, Gls2, Acot8, Tmlhe, Af6, F2, Ywag, PPAR A, Resp18, Edn1 and oxytocin).

TABLE 1

Gene Expression at 2 weeks post MI

| Gene | Captopril v Control | Placebo v Control | Captopril v Placebo |
|---|---|---|---|
| MIR16 | ↔ | ↓21 ± 3% | ↑37 ± 3% |
| IL-1β | ↑410 ± 90% | ↑390 ± 12% | ↔ |
| Agt | ↑129 ± 10% | ↑44 ± 15% | ↑59 ± 7% |
| Cxcl12 | ↑116 ± 11% | ↑50 ± 12% | ↑45 ± 7% |
| Sel1h | ↑64 ± 7% | ↑38 ± 12% | ↔ |
| Acot8 | ↓41 ± 8% | ↓51 ± 2% | ↔ |
| Cox5a | ↓158 ± 3% | ↓45 ± 5% | ↔ |
| HGF | ↓32 ± 3% | ↓35 ± 3% | ↔ |

Control = uninfarcted baseline control
Captopril = post MI with captopril therapy
Placebo = post MI with placebo
↑ = up regulation (in %, mean ± SEM) or significant (P < 0.05)
↓ = down regulation (in %)
↔ = no significant change in expression (significant = P < 0.05)
MIR16, membrane interacting protein of RGS16; IL-1β, interleukin 1 beta; Agt, angiotensinogen; Cxcl12, chemokine (C-X-C motif) ligand 12; Sel1h, suppressor of lin-12 1 homolog; Acot8, acyl-CoA thioesterase 8; Cox5a, cytochrome c oxidase, subunit Va; HGF, hepatocyte growth factor.

At 4 weeks post MI (Table 2) a similar analysis demonstrated a significant change in expression of 8 genes in the post-MI groups compared to uninfarcted control aorta. In particular, expression of IL-1β, Fmr1, and Rock2 was significantly increased in the placebo treated group, expression of Taok1, Raf1, Baat, and Gls2 was decreased by captopril therapy, and expression of Acot8 was depressed in both post-MI groups. Comparing the two post-MI groups, captopril therapy significantly reduced expression of Taok1, Raf1, IL-1β, Fmr1, Rock2, Baat, and Gls2. At 4 weeks post infarction, there was no significant change in the expression of 14 genes (MIR16, Agt, Cxcl12, Seh1h, Cox5, HGF, Tmlhe, Af6, F2, Ywag, PPAR A, Resp18, Edn1 and oxytocin).

TABLE 2

Gene Expression at 4 weeks post MI

| Gene | Captopril v Control | Placebo v Control | Captopril v Placebo |
|---|---|---|---|
| Taok1 | ↓21 ± 3% | ↔ | ↓31 ± 2% |
| Raf1 | ↓29 ± 1 | ↔ | ↓35 ± 1 |
| IL-1β | ↔ | ↑340 ± 140 | ↓71 ± 5 |
| Fmr1 | ↔ | ↑49 ± 18 | ↓36 ± 2 |
| Rock2 | ↔ | ↑54 ± 18 | ↓37 ± 8 |
| Baat | ↓94 ± 1 | ↔ | ↓95 ± 1 |
| Gls2 | ↓40 ± 4 | ↔ | ↓40 ± 4 |
| Acot8 | ↓43 ± 8% | ↓53 ± 3% | ↔ |

Control = uninfarcted baseline control
Captopril = post MI with captopril therapy
Placebo = post MI with placebo
↑ = up regulation (in %, mean ± SEM) or significant ($P < 0.05$)
↓ = down regulation (in %)
↔ = no significant change in expression (significant = $P < 0.05$)
Taok1, TAO kinase 1; Raf1, v-raf-1 murine leukemia viral oncogene homolog 1; IL-1β, interleukin 1 beta; Fmr1, fragile X mental retardation syndrome 1 homolog; Rock2, Rho kinase 2; Baat, bile acid-Coenzyme A amino acid N-acyltransferase; Gls2, glutaminase 2 (liver, mitochondrial); Acot8, acyl-CoA thioesterase 8;

For the 22 genes targeted for testing in aortic tissue with respect to captopril therapy, the expression of 10 genes changed between 2 and 4 weeks post-infarction. Three genes (MIR16, Agt, and Cxcl12) initially had increased expression at 2 weeks, but the difference disappeared by 4 weeks (FIG. 1). In addition, for seven genes (Taok1, Raf1, IL1-β, Fmr1, Rock2, Baat, and Gls2) that initially did not demonstrate any difference in expression between placebo or captopril therapy at 2 weeks, expression fell with captopril treatment at 4 weeks post-infarction (FIG. 1).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for evaluating the prognosis of a subject with a chronic disease where there is vascular dysfunction, comprising providing a biological sample from said subject, performing an ELISA to measure in said biological sample the expression level of TAO kinase I, glutaminase 2 (Gls2), v-raf-1 murine leukemia viral oncogene homolog 1 (Raf1), or bile acid-Coenzyme A amino acid N-acyltransferase (Baat), and classifying the prognosis of the subject as favorable if the expression level of TAO kinase I, Gls2, Raf1, or Baat in the biological sample is less than a control expression level of TAO kinase I, Gls2, Raf1, or Baat, or classifying the prognosis of the subject as poor if the expression level of TAO kinase I, Gls2, Raf1, or Baat in the biological sample is not less than the control expression level of TAO kinase I, Gls2, Raf1, or Baat and wherein the control expression level is an expression level in a biological sample from a normal subject, a standard expression level in biological samples from a population of normal subjects, or a previously determined expression level in a biological sample from the subject.

2. The method of claim 1, wherein the disease is chronic heart failure (CHF).

3. A method for evaluating the prognosis of a subject with a chronic disease where there is vascular dysfunction, comprising providing a biological sample from said subject, performing an ELISA to measure in said biological sample the expression level of interleukin-1β (IL-1β), Rho kinase 2, or fragile X mental retardation syndrome 1 homolog (Fmr1), and classifying the prognosis as favorable if the expression level of IL-1β, Rho kinase 2, or Fmr1 in the biological sample is similar to or less than a control expression level of IL-1β, Rho kinase 2, or Fmr1, or classifying the prognosis as poor if the expression level of IL-1β, Rho kinase 2, or Fmr1 in the biological sample is greater than the control expression level of IL-1β, Rho kinase 2, or Fmr1, and wherein:
the control expression level is an expression level of IL-1β, Rho kinase 2, or Fmr1 in a biological sample from a normal subject, or a standard expression level of IL-1β, Rho kinase 2, or Fmr1 in biological samples from a population of normal subjects, and the prognosis is classified as favorable if the expression level in the biological sample is similar to the control expression level, or classified as poor if the expression level in the biological sample is greater than the control expression level, or
the control expression level is a previously determined expression level of IL-1β, Rho kinase 2, or Fmr1 in a biological sample from the subject, and the prognosis is classified as favorable if the expression level in the biological sample is less than the control expression level, or classified as poor if the expression level in the biological sample is similar to or greater than the control expression level.

4. The method of claim 3, wherein the disease is CHF.

5. The method of claim 3, wherein the control expression level is an expression level of IL-1β, Rho kinase 2, or Fmr1 in a biological sample from a normal subject, or a standard expression level of IL-1β, Rho kinase 2, or Fmr1 in biological samples from a population of normal subjects, wherein the prognosis is classified as favorable if the expression level in the biological sample is similar to the control expression level, and wherein the prognosis is classified as poor if the expression level in the biological sample is greater than the control expression level.

6. The method of claim 3, wherein the control expression level is a previously determined expression level of IL-1β, Rho kinase 2, or Fmr1 in a biological sample from the subject, wherein the prognosis is classified as favorable if the expression level in the biological sample is less than the control expression level, and wherein the prognosis is classified as poor if the expression level in the biological sample is similar to or greater than the control expression level.

7. A method for assessing the response to treatment of a subject diagnosed as having a chronic disease where there is vascular dysfunction, the method comprising:
(a) providing a biological sample from said subject;
(b) performing an ELISA to measure the expression level of a gene in said biological sample, wherein the gene is TAOK1, GLS2, RAF1, or BAAT; and
(c) classifying the response as favorable if the expression level in the biological sample is less than a control expression level of the gene, or classifying the response as poor if the expression level in the biological sample is not less than the control expression level of the gene, wherein the control expression level is an expression level in a biological sample from a normal subject, a standard expression level in biological samples from a population of normal subjects, or a previously determined expression level in a biological sample from the subject.

8. The method of claim 7, wherein the disease is CHF.

9. The method of claim 7, wherein the treatment is captopril therapy.

10. A method for assessing the response to treatment of a subject diagnosed as having a chronic disease where there is vascular dysfunction, the method comprising:
   (a) providing a biological sample from said subject;
   (b) performing an ELISA to measure the expression level of a gene in said biological sample, wherein the gene is IL-1β, ROCK2, or FMR1; and
   (c) classifying the response as favorable if the expression level in the biological sample is similar to or less than a control expression level of the gene, or classifying the response as poor if the expression level in the biological sample is greater than the control expression level of the gene, wherein:
   the control expression level is an expression level in a biological sample from a normal subject, or a standard expression level in biological samples from a population of normal subjects, and the response is classified as favorable if the expression level in the biological sample is similar to the control expression level of the gene, or classified as poor if the expression level in the biological sample is greater than the control expression level of the gene, or
   the control expression level is a previously determined expression level in a biological sample from the subject, and the response is classified as favorable if the expression level in the biological sample is less than the control expression level of the gene, or classified as poor if the expression level in the biological sample is similar to or greater than the control expression level of the gene.

11. The method of claim 10, wherein the disease is CHF.

12. The method of claim 10, wherein the control expression level is an expression level in a biological sample from a normal subject, or a standard expression level in biological samples from a population of normal subjects, wherein the response is classified as favorable if the expression level in the biological sample is similar to the control expression level of the gene, and wherein the response is classified as poor if the expression level in the biological sample is greater than the control expression level of the gene.

13. The method of claim 10, wherein the control expression level is a previously determined expression level in a biological sample from the subject, wherein the response is classified as favorable if the expression level in the biological sample is less than the control expression level of the gene, and wherein the response is classified as poor if the expression level in the biological sample is similar to or greater than the control expression level of the gene.

14. The method of claim 10, wherein the treatment is captopril therapy.

15. A method for evaluating the prognosis of a subject with a chronic disease where there is vascular dysfunction, comprising providing a biological sample from said subject, performing an ELISA to measure in said biological sample the expression level of membrane interacting protein RGS16 (Mir16), angiotensinogen (Agt), or chemokine (C-X-C motif) ligand 12 (Cxcl12), and classifying the prognosis of the subject as favorable if the expression level of Mir16, Agt, or Cxcl12 in the biological sample is greater than or similar to a control expression level of Mir16, Agt, or Cxcl12, or classifying the prognosis as poor if the expression level of Mir16, Agt, or Cxcl12 in the biological sample is less than the control expression level of Mir16, Agt, or Cxcl12, and wherein:
   the control expression level is an expression level of Mir16, Agt, or Cxcl12 in a biological sample from a normal subject, or a standard expression level of Mir16, Agt, or Cxcl12 in biological samples from a population of normal subjects, and the prognosis is classified as favorable if the expression level in the biological sample is similar to the control expression level, or classified as poor if the expression level in the biological sample is less than the control expression level, or
   the control expression level is a previously determined expression level of Mir16, Agt, or Cxcl12 in a biological sample from the subject, and the prognosis is classified as favorable if the expression level in the biological sample is greater than the control expression level, or classified as poor if the expression level in the biological sample is less than or similar to the control expression level.

16. The method of claim 15, wherein the disease is CHF.

17. The method of claim 15, wherein the control expression level is an expression level of Mir16, Agt, or Cxcl12 in a biological sample from a normal subject, or a standard expression level of Mir16, Agt, or Cxcl12 in biological samples from a population of normal subjects, wherein the prognosis is classified as favorable if the expression level in the biological sample is similar to the control expression level, and wherein the prognosis is classified as poor if the expression level in the biological sample is less than the control expression level.

18. The method of claim 15, wherein the control expression level is a previously determined expression level of Mir16, Agt, or Cxcl12 in a biological sample from the subject, wherein the prognosis is classified as favorable if the expression level in the biological sample is greater than the control expression level, and wherein the prognosis is classified as poor if the expression level in the biological sample is less than or similar to the control expression level.

19. A method for assessing the response to treatment of a subject diagnosed as having a chronic disease where there is vascular dysfunction, the method comprising:
   (a) providing a biological sample from said subject;
   (b) performing an ELISA to measure the expression level of a gene in said biological sample, wherein the gene is MIR16, AGT, or CXCL12; and
   (c) classifying the response as favorable if the expression level in the biological sample is similar to or greater than a control expression level of the gene, or classifying the response as poor if the expression level in the biological sample is less than the control expression level of the gene, wherein:
   the control expression level is an expression level in a biological sample from a normal subject, or a standard expression level in biological samples from a population of normal subjects, and the response is classified as favorable if the expression level in the biological sample is similar to the control expression level of the gene, or classified as poor if the expression level in the biological sample is less than the control expression level of the gene, or
   the control expression level is a previously determined expression level in a biological sample from the subject, and the response is classified as favorable if the expression level in the biological sample is greater than the control expression level of the gene, or classified as poor if the expression level in the biological sample is similar to or less than the control expression level of the gene.

20. The method of claim 19, wherein the disease is CHF.

21. The method of claim 19, wherein the control expression level is an expression level in a biological sample from a normal subject, or a standard expression level in biological samples from a population of normal subjects, wherein the response is classified as favorable if the expression level in the biological sample is similar to the control expression level of the gene, and wherein the response is classified as poor if the expression level in the biological sample is less than the control expression level of the gene.

22. The method of claim 19, wherein the control expression level is a previously determined expression level in a biological sample from the subject, wherein the response is classified as favorable if the expression level in the biological sample is greater than the control expression level of the gene, and wherein the response is classified as poor if the expression level in the biological sample is similar to or less than the control expression level of the gene.

23. The method of claim 19, wherein the treatment is captopril therapy.

* * * * *